United States Patent
Payzant et al.

(10) Patent No.: US 6,777,480 B2
(45) Date of Patent: Aug. 17, 2004

(54) NETWORKED POLYMER/CLAY ALLOY

(75) Inventors: John Donald Payzant, Edmonton (CA); Zhihong Zhou, Edmonton (CA)

(73) Assignee: Alberta Research Council Inc., Edmonton (CA)

( * ) Notice: Subject to any disclaimer, the term of this patent is extended or adjusted under 35 U.S.C. 154(b) by 0 days.

(21) Appl. No.: 10/397,594

(22) Filed: Mar. 26, 2003

(65) Prior Publication Data

US 2003/0191237 A1 Oct. 9, 2003

Related U.S. Application Data

(63) Continuation of application No. 09/579,547, filed on May 26, 2000, now Pat. No. 6,610,780, which is a continuation-in-part of application No. 09/356,164, filed on Jul. 16, 1999, now abandoned.

(30) Foreign Application Priority Data

May 26, 1999 (CA) .............................................. 2272965

(51) Int. Cl.$^7$ ................................................ C08K 3/34

(52) U.S. Cl. ........................ 524/445; 524/447; 524/789; 524/790

(58) Field of Search ................................. 524/445, 447, 524/789, 790

(56) References Cited

U.S. PATENT DOCUMENTS 4,977,192 A * 12/1990 Martineu et al. .............. 521/56
6,602,933 B2 * 8/2003 Tang et al. .................. 523/212

FOREIGN PATENT DOCUMENTS

JP          05-287271       * 11/1993

* cited by examiner

*Primary Examiner*—Helen L. Pezzuto
(74) *Attorney, Agent, or Firm*—Kurt D. Van Tassel; Deborah G. VandenHoff; Van Tassel & Associates

(57) ABSTRACT

A networked polymer/clay alloy is produced from a monomer/clay mixture comprising a monomer, a cross-linking agent and clay particles. An initiator means is used to initiate polymerization of the monomer/clay mixture. The clay is chemically integrated with the polymer such that, on exposure to water, the networked polymer/clay alloy swells with substantially no clay separating from the alloy.

22 Claims, 7 Drawing Sheets

NETWORKED POLYMER/CLAY ALLOY

This application is a continuation of U.S. patent application Ser. No. 09/579,547 filed in the names of John Donald Payzant and Zhihong Zhou on May 26, 2000, now U.S. Pat. No. 6,610,780 which is a continuation-in-part of U.S. patent application Ser. No. 09/356,164 filed Jul. 16, 1999, abandoned.

FIELD OF THE INVENTION

The present invention relates to an absorbent polymer and a process for making an absorbent polymer. More specifically, the present invention relates to a networked polymer/clay alloy useful for example, without limitation, in containment applications as landfill liners or covers, reservoir liners, underground storage tank liners, secondary containment liners, and man-made bodies of water, or personal care absorbent articles, including diapers, training pants, feminine hygiene products such as sanitary napkins, incontinence devices and the like.

BACKGROUND DISCUSSION

Super absorbent polymers ("SAPs") have been produced since the 1970s for use in a variety of products including, amongst others, hygiene products, such as disposable diapers, training pants, feminine hygiene products and incontinence devices, agricultural and horticultural products and industrial and environmental absorbents. SAPs are primarily utilized to increase or enhance the product's water-absorbency.

SAPs are produced from a variety of components by a variety of processes. For example, SAPs are often made from monomers such as acrylamide, acrylic acid and acrylate, which are particularly suitable for application in hygiene products.

For example, U.S. Pat. No. 4,032,701 (Hughes, Jun. 28, 1977) describes a process for producing polyacrylamide in dry and solid form using a polymerization catalyst selected from a group consisting of an alkali metal and ammonium sulfite, bisulfite and persulfate. U.S. Pat. No. 4,178,221 (Boutin et al, Dec. 11, 1979) describes a process for producing water-soluble acrylic polymers using a sequential photopolymerization technique. Photopolymerization promoters are incorporated in the monomer solution to facilitate polymerization. U.S. Pat. No. 4,283,517 (Perricone et al, Aug. 11, 1981) produces polyacrylamide using a quaternary ammonium salt as a cross-linking agent, while U.S. Pat. No. 4,295,987 (Parks, Oct. 20, 1981) uses two cross-linking agents to produce a cross-linked sodium polyacrylate absorbent.

Further examples of the production of SAPs providing improved properties are provided by U.S. Pat. No. 4,731,067 (Le-Khac, Mar. 15, 1988), U.S. Pat. No. 5,185,409 (Sortwell, Feb. 9, 1993), U.S. Pat. No. 5,145,906 (Chambers et al, Sep. 8, 1992), U.S. Pat. No. 5,462,972 (Smith et al, Oct. 31, 1995), U.S. Pat. No. 5,672,633 (Brehm et al, Sep. 30, 1997) and U.S. Pat. No. 5,858,535 (Wang et al, Jan. 12, 1999).

The SAP produced by each of the above-noted patents is manufactured from a chemical monomer to produce a synthetic polymer. Such chemical monomers tend to be relatively expensive and therefore, the use of the SAP produced therefrom tends to be limited to applications requiring a relatively small amount of SAP. For example, SAP made from chemical monomers tends to be too expensive for use in environmental applications given the large volumes that are typically required. The most significant expense in producing SAP is the cost of the chemical monomer. In addition, these synthetic polymers may be subject to chemical, electromagnetic (radiation) and biological (bacterial) degradation when placed in the surface environment.

Alternately, swelling clays may be used to provide water-absorbency to a product. With respect to cost, the cost of swelling clays tends to be minimal compared to that of the chemical monomers described above. In addition, swelling clays are relatively stable compared to chemical monomers and are not as subject to degradation. However, swelling clays have a water absorption capacity significantly less than that of SAP.

Thus, in order to reduce the cost of producing SAP and address the problems associated with using SAP in some applications, the polymers may be physically mixed into swelling clays to form a composite. Alternately, the monomers may be intercalated in the swelling clays and polymerized into a nanocomposite. In either event, the incorporation of the swelling clays into the SAP reduces the total cost of the SAP and enhances its resistance to chemical, electromagnetic and biological degradation, while still providing an improved water absorption capacity as compared to that of the swelling clays alone.

As indicated one technique for producing the improved SAP is to physically mix the polymer or otherwise intercalate or combine the polymer with the swelling clay to produce a water absorbent composite. For example, U.S. Pat. No. 4,418,163 (Murakami et al, Nov. 29, 1983) describes a method of making a water absorbing composite that is comprised of an inorganic powder and an absorbent resin covering the surfaces of the individual particles of the inorganic powder. The inorganic powder is white carbon, synthetic silicate white carbon, basic magnesium carbonate, ultrafine magnesium silicate, light and heavy calcium carbonate, soft and hard clay, talc, vermiculite, pearlite, barium sulfate (baryte) or mica. Thus, this patent describes a process for coating an inorganic powder with a polymer. Similar processes are described in U.S. Pat. No. 4,889,885 (Usuki et al, Dec. 26, 1989) and U.S. Pat. No. 5,352,287 (Wason et al, Oct. 4, 1994).

An alternative technique for producing the improved SAP is to polymerize an intercalated monomer. For example, Blumstein, R. et al (Applied Polymer Symposium 25: 81–88; 1974) prepares a clay-polymer complex with monolayers between the structural layers of clay minerals, namely montmorillonite clay. Specifically, clay-monomer complexes, of nearly monolayer coverage, are polymerized through free radical initiation with γ-ray irradiation to produce clay-polymer complexes. Blumstein, A. (Journal of Polymer Science: Part A, 3:2653–2661; 1995) similarly describes the polymerization of monolayers of an acrylic monomer adsorbed on the surface of the clay, namely montmorillonite, initiated with γ-ray irradiation or by free radical catalysts.

Similarly, Chinese Patent No. 85-1-02156-A (Jan. 14, 1987) describes a method of preparing a bentonite-acrylamide based SAP using cobalt-60 γ-ray irradiation. Specifically, the Chinese patent uses γ-ray irradiation to initialize polymerization. As well, Nagae H. et al (Kobunshi Ronbun 47:8:631–638; 1990) describes the preparation of complex composite films by adding acrylamide and water to montmorillonite and polymerizing the product using γ-ray irradiation. Thus, as with Blumstein, each of these processes requires an irradiation source for polymerization.

Further, Ogawa M. et al, (*Clay Science* 7:243–251; 1989) describes the preparation of montmorillonite-polyacrylamide intercalation compounds by polymerizing the intercalated acrylamide monomers in the interlayer region of the montmorillonite using a free radical initiator. The polymerization is performed using a relatively complex process involving the use of an organic solvent, namely n-heptane. First, the montmorillonite is intercalated into an acrylamide aqueous solution. The product is then dried and washed with an organic solvent, namely $CCl_4$ or n-heptane, to remove excess acrylamide. Finally, the intercalated acrylamide is polymerized by heating the intercalation compounds with benzoyl peroxide as an initiator in n-heptane.

Kato, C. et al (*Clays and Clay Minerals* 29:4:294–298; 1981) describes the polymerization of intercalation compounds of styrene and ammonium montmorillonite. Specifically, clay suspensions, namely montmorillonite, are mixed with ammonium solutions. After washing and drying the resulting product, the dried organoammonium-montmorillonites are immersed in styrene monomer. The resulting stearyltrimethylammonium-montmorillonite is dried and polymerized using benzoyl peroxide as an initiator.

It would be desirable to produce an absorbent material having intimately integrated components that do not disperse and/or migrate from the product.

SUMMARY OF THE INVENTION

According to the invention, there is provided a process for producing a networked polymer/clay alloy, comprising the steps of: (a) preparing a monomer/clay mixture by mixing at least a monomer, clay particles, a cross-linking agent, and a mixing fluid in a vessel; (b) exposing the monomer/clay mixture to a thermal initiator means comprising at least one thermal initiator and thermal energy, wherein exposing the monomer/clay mixture to the thermal initiator means comprises: (i) mixing, in any order, the at least one thermal initiator with at least the monomer, clay particles, the cross-linking agent and the mixing fluid so that a monomer/clay mixture is exposed to the thermal initiator; (ii) exposing the monomer/clay mixture to a thermal energy source at a temperature in a range from about 40° C. to about 95° C.; and (c) polymerizing the monomer/clay mixture so that a networked polymer/clay alloy is formed.

BRIEF DESCRIPTION OF THE DRAWINGS

The networked polymer/clay alloy and the process for producing the networked polymer/clay alloy of the present invention will be better understood by referring to the following detailed description of preferred embodiments and the drawings referenced therein, in which.

DETAILED DESCRIPTION OF PREFERRED EMBODIMENTS

Definitions

Figure 1:
FIG. 1 is a scanning electron microscope (SEM) micrograph of a top plan perspective of the reinforcing agent used in Example 3, at a magnification of 140×.

"Monomer" is an organic molecule that can combine with a number of the same or different molecules to form a large molecule having repeating monomeric units, wherein the repeating monomeric units have a similar chemical architecture and atom composition as the monomeric units.

"Polymer" is a large molecule built from the same or different repeating monomeric units and typically has a molecular weight in a range from about 10,000 to about 20,000,000. Polymer, as used herein, also includes any polymer made from two or more different repeating units, such as copolymers (i.e., comprising two different monomeric units), terpolymers (i.e., comprising three different monomeric units), tetrapolymers (i.e., comprising four different monomeric units) and so on. Moreover, the repeating monomeric units can alternate in a sequential pattern (e.g., A-B-A-B), block pattern (e.g., A-A-B-B), random pattern (A-B-B-A-B-A) or combinations thereof.

"Oligomer" is also built from the same or different repeating monomer units but is a smaller molecule than a polymer and typically has a molecular weight in a range of from about 200 up to about 9,000.

"Polymerization Initiator Means" is a chemical substance, gamma ray irradiation, X-ray irradiation, irradiation by high energy sub-atomic particles, each type of radiation having a wavelength less than about 10 nm, (collectively, high energy irradiation) and combinations thereof that can increase the reactivity of a monomer so that a polymerization or oligomerization chain reaction between monomers is initiated and a polymer or oligomer is formed. At the appropriate temperature, certain chemical substances become either an ionic or free radical species that can react with a monomer alone to produce an ionic or free radical monomeric species, which can, in turn, react with another monomer, thereby initiating a polymerization reaction. Also, high energy irradiation can be used to produce an ionic or free radical monomeric species from a monomer and/or a chemical substance other than a monomer to initiate a polymerization reaction.

"Cross-linking Agent" is a chemical substance, photons produced from a radiation source and combinations thereof that assist in forming a bridging moiety between two or more backbone structures formed by multiple monomeric units (e.g., oligomeric or polymeric units). Thus, a cross-linking agent can bridge oligomeric or polymeric species either during or after their formation.

"Networked Polymer" is a very large polymer molecule formed by cross-linking multiple oligomers and/or polymers to form an interconnected polymeric network. A networked polymer can have cross-linking moieties between oligomers and/or polymers, where the moieties are formed from either the cross-linking agent itself, branches attached to the backbone of each oligomer and/or polymer or combinations thereof.

"Networked Polymer/Clay Alloy" ("NPC Alloy") is a chemically integrated composition of polymer and clay. Clay particles form a unique chemical association with the networked polymer as it is formed. The chemical association may be, for example, without limitation, through hydrogen bonding, ionic bonding, Van der Waal's/dipole bonding, affinity bonding, covalent bonding and combinations thereof.

General Discussion

An NPC alloy of the present invention is an absorbent material useful, for example, without limitation, for making fluid barriers, such as landfill liners or covers, reservoir liners, underground storage tank liners, secondary containment liners, and liners for man-made bodies of water, or personal care absorbent articles, including diapers, training pants, feminine hygiene products such as sanitary napkins, incontinence devices and the like.

In containment applications, the alloy preferably absorbs water to form a barrier, which then has a relatively low permeability to water, oil and other liquids. In personal care articles, the alloy preferably has a high water absorbency capacity. As discussed more fully below, the properties of the NPC alloy can be adjusted depending on the application.

The NPC alloy of the present invention has improved resistance to chemical, electromagnetic radiation and biological degradation in surface and subsurface conditions. By improved resistance to chemical degradation, we mean that the alloy has improved resistance to, for example, without limitation, salt water and drainage fluids with high heavy metal content and/or acidic pH. By improved resistance to electromagnetic degradation, we mean that the composite has an improved resistance to ultraviolet (UV) and other potentially detrimental electromagnetic radiation. By improved resistance to biological degradation, we mean that the NPC alloy would be more resistant to bacterial attack after installation, as compared with a polymer without clay.

For example, the permeability of a liner produced with the NPC alloy is not significantly affected by salt water, or other aqueous solutions with heavy metals and/or acidic pH. Thus, a liner produced with the NPC alloy represents an improvement over a conventional geosynthetic clay liner ("GCL"), which typically loses its effectiveness on exposure to salt water.

As another example, polyacrylamide is stable at surface and sub-surface conditions. However, it is susceptible to chemical and UV degradation. The clay reduces degradation in the NPC alloy by protecting the polymer. Also, the NPC alloy is more resistant to biological degradation than, for example, polyacrylic acid alone.

When used in barrier applications, the NPC alloy weighs less than a comparably effective clay loading for a conventional GCL per unit area. Also, a liner produced with the NPC alloy can be used without pre-hydration, as is often required for conventional GCL's.

An NPC alloy is produced by mixing a monomer, clay particles, a cross-linking agent and a mixing fluid. The monomer/clay mixture is exposed to an initiator means to initiate polymerization to form a networked polymer/clay alloy.

The polymer and clay in the NPC alloy cooperate physically and chemically (i.e., physicochemically) to contribute to the alloy's water absorbency. Thus, the alloy can swell while only negligible amounts of clay, if any, (i.e., substantially no clay) separate from the composite when it is immersed in deionized water at temperatures in a range of from about 1° C. to about 60° C.

Monomer/Clay Mixture

The monomer/clay mixture used in making the NPC alloy includes, without limitation, a monomer, clay particles, a cross-linking agent and a mixing fluid. For brevity, we may refer to the mixture of monomer, clay, cross-linking agent and mixing fluid as "MCX."

The monomer is at least partially soluble in the mixing fluid. A monomer soluble in the mixing fluid may be mixed with other monomers that are soluble or insoluble in the mixing fluid. Preferably, at least one water-soluble monomer has the following general formula:

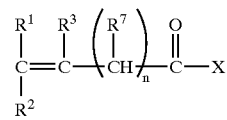

wherein X is selected from the group consisting of OM, $OR^4$ and $NR^5R^6$, M is an alkali or alkaline earth metal ion or $NH_4^+$, $R^1$, $R^2$, $R^3$, $R^5$, $R^6$ and $R^7$ are independently selected from the group consisting of H, $CH_3$, $CH_2CH_3$, $CH_2CH_2CH_3$, $CH(CH_3)_2$, $CH_2CH_2CH_2CH_3$, and CN, and $OR^4$ is selected from the group consisting of OH, $OCH_3$, $OCH_2CH_3$, $OCH_2CH_2CH_3$, $OCH(CH_3)_2$, $OCH_2CH_2CH_2CH_3$, $OCH_2CH_2OH$ and $(OCH_2CH_2)_mOH$, n=0 to about 10 and m=1 to about 10.

More preferably, the monomer is selected from the group consisting of acrylic acid (where $R^1$=H, $R^2$=H, $R^3$=H, n=0, X=$OR^4$, $R^4$=H), acrylamide (where $R^1$=H, $R^2$=H, $R^3$=H, n=0, X=$NR^5R^6$, $R^5$=H, $R^6$=H), sodium acrylate (where $R^1$=H, $R^2$=H, $R^3$=H, n=0, X=OM, M=Na), potassium acrylate (where $R^1$=H, $R^2$=H, $R^3$=H, n=0, X=OM, M=K), methacrylic acid (where $R^1$=H, $R^2$=H, $R^3$=$CH_3$, n=0, X=$OR^4$, $R^4$=H), N-isopropylacrylamide (where $R^1$=H, $R^2$=H, $R^3$=H, n=0, X=$NR^5R^6$, $R^5$=$CH(CH_3)_2$, $R^6$=H), and combinations thereof.

An example of a monomer that can be co-polymerized with a monomer of the above general formula are vinyl esters, such as vinyl acetate. Vinyl acetate is readily co-polymerized and may be retained as a vinyl acetate moiety or subsequently hydrolyzed to the corresponding vinyl alcohol.

The clay particles may be swelling or non-swelling clays. Suitable swelling clay particles include, without limitation, montmorillonite, saponite, nontronite, laponite, beidellite, iron-saponite, hectorite, sauconite, stevensite, vermiculite, and combinations thereof. Suitable non-swelling clay particles include, without limitation, kaolin minerals (including kaolinite, dickite and nacrite), serpentine minerals, mica minerals (including illite), chlorite minerals, sepiolite, palygorskite, bauxite, silica and combinations thereof.

Preferably, the clay is a swelling clay such as, for example, smectite and vermiculite type clays. More preferably, the clay is a smectite type clay. Examples of suitable smectites are, without limitation, montmorillonite (sometimes referred to as bentonite), beidellite, nontronite, hectorite, saponite, sauconite and laponite. Bentonite is an example of a naturally-occurring combination of clay particles. Bentonite is a rock rich in montmorillonite and may also comprise other smectites as well as other non-clay mineral constituents. Consequently, montmorillonites or their mixtures with other smectites are often referred to simply as bentonite. Bentonite clays are fine crystals or particles, usually plate-like in shape, with a lateral dimension up to 2 $\mu$m and a thickness in a range of a few to tens of nanometers (nm).

Swelling clays have the ability to absorb water and are less expensive than monomer. Accordingly, the reinforced networked polymer composite of the present invention is less expensive than one produced without clay. Moreover, clay particles are resistant to degradation in long-term environmental applications, while still providing water absorbency for long periods of time.

Non-swelling clays would provide increased resistance to salt water for the NPC alloy. Also, non-swelling clays, like swelling clays, are less expensive than monomer and would reduce an application's cost.

Preferably, the weight ratio of clay to monomer in the MCX mixture is in a range of from about 0.05:1 to about 19:1. More preferably, the weight ratio of clay to monomer in the MCX mixture is in a range of from about 0.5:1 to about 3:1.

Suitable chemical substances for use as cross-linking agents include, without limitation, N,N'-methylene bisacrylamide, phenol formaldehyde, terephthalaldehyde, allylmethacrylate, diethyleneglycol diacrylate, ethoxylated trimethylolpropane triacrylate, ethylene carbonate, ethylene glycol diglycidal ether, tetraallyloxyethane, triallylamine, trimethylolpropanetriacrylate, and combinations thereof.

As a general rule, depending on the selected polymerization reaction time and temperature, a higher ratio of cross-linking agent to monomer will generally produce a lower concentration of residual monomer, but the networked polymer's water absorption capacity (WAC) may drop if the ratio gets too high. The weight ratio of the cross-linking agent to the monomer is preferably in a range of from about 0.05:100 to about 1.5:100. More preferably, the weight ratio of the cross-linking agent to the monomer is in a range of from about 0.05:100 to about 0.7:100. Most preferably, the weight ratio of the cross-linking agent to the monomer is in a range of from about 0.1:100 to about 0.5:100.

The mixing fluid is a polar solvent. Examples of suitable mixing fluids include, without limitation, water, alcohol, oxygen-containing organic solvents, and combinations thereof, in which the monomer can be at least partially dissolved. Examples of suitable oxygen-containing organic solvents include, without limitation, alcohols, glycols, polyols, sulfoxides, sulfones, ketones and combinations thereof. Preferably, the mixing fluid is water, alcohol or a combination thereof. Most preferably, the mixing fluid is water.

Preferably, the amount of mixing fluid in the MCX mixture is in a range of from about 30% to about 90% by weight. More preferably, the amount of mixing fluid in the MCX mixture is in a range of from about 40% to about 80% by weight. Most preferably, the amount of mixing fluid in the MCX mixture is in a range of from about 40% to about 60% by weight.

Additionally, the MCX mixture preferably comprises one or more additives. Buffering agents and/or neutralizing agents may be used as additives to maintain the pH of the mixture in a predetermined range and/or neutralize acidic and/or basic monomers.

Also, metal complexing agents may be used as additives to form metal complexes, thereby sequestering metal ions that might otherwise interfere with forming the NPC alloy. For example, acrylamide monomer is typically manufactured with cupric salts as a stabilizer (e.g., to inhibit polymerization during shipment or in storage). Thus, a metal complexing agent, such as a sodium carbonate or ethylenediaminetetracetic acid (EDTA), can be added to the MCX mixture to complex the metal ion and thereby sequester the metal. It should be understood that some additives can be used to satisfy multiple functions. For example, sodium carbonate ($Na_2CO_3$) and sodium bicarbonate ($NaHCO_3$), could function as both a buffering agent (i.e., maintaining pH) and a neutralizing agent (i.e., neutralizing acidic monomers), while also working as a metal complexing agent. Therefore, it will be apparent to those skilled in the art that one or more additives can be used for forming an NPC alloy depending on the monomer and cross-linking agent used, type of stabilizing agent mixed with the monomer, type of polymerization reaction and the desired reaction pH and temperature.

Examples of buffering agents and/or neutralizing agents include, without limitation, sodium hydroxide, potassium hydroxide, ammonium hydroxide, sodium carbonate, sodium bicarbonate, potassium carbonate, potassium bicarbonate, oxylate-containing compounds, sulfate-containing compounds, phosphate-containing compounds, and combinations thereof.

Examples of metal complexing agents include, without limitation, sodium carbonate, sodium bicarbonate, potassium carbonate, potassium bicarbonate, ethylenediaminetetraacetic acid (EDTA), EDTA salts, orthophosphate, pyrophosphate, metaphosphate, hydrogen phosphate, and combinations thereof.

Each of the components of the MCX mixture may be added in any order. Preferably, however, the mixing fluid and monomer are mixed with any other desired component, followed by adding a chemical initiator and then adding the clay. Also, caution should be exercised in mixing any mixture components to avoid any significant exotherms. Otherwise, any significant exotherm should be allowed to cool. A large exotherm from mixing components might otherwise lead to premature polymerization shortly after the initiator is added, but before the mixture is heated under a controlled condition.

The MCX mixture forms a slurry type mixture, which should be mixed until it is substantially homogeneous.

Polymerization

An NPC alloy is produced by polymerization of the MCX mixture while the cross-linking agent, acting in concert with the polymerization process, helps to form a networked polymer/clay alloy structure. Polymerization of the MCX mixture is initiated by a polymerization initiator means for generating an ionic or free radical monomeric species. Initiation may be accomplished by adding a suitable chemical substance to the MCX mixture. Also, electromagnetic radiation having a wavelength of 10 nanometers (nm) or less may be used alone or in combination with a chemical initiator.

Suitable chemical substances for initiating polymerization include, without limitation, free radical initiators, carbanions, carbonium ions, and combinations thereof.

Examples of free radical initiators include, without limitation, thermal initiators, and redox systems, which are typically two or more chemicals, which are added simultaneously as different solutions.

Examples of thermal initiators include, without limitation, (1) alkali metal salts of sulfite, bisulfite, persulfate, benzoyl peroxide, and combinations thereof, (2) ammonium salts of sulfite, bisulfite, persulfate, benzoyl peroxide, and combinations thereof, (3) 2,2'-azobis(2-amidino-propane)-dihydrochloride, (4) 2,2'-azobis(4-cyanopentanoic acid), and combinations thereof.

The desired polymerization temperature for forming an NPC alloy composite is primarily dependent on the type and concentration of initiator means selected. For example, lower polymerization temperatures may be used where a thermal initiator prone to forming free radicals at a lower temperature (e.g., about 40° C. to about 50° C.) is used. Thus, where the polymerization reaction used for making the NPC alloy is initiated with a thermal initiator, the reaction is preferably at a temperature in a range of from about 40° C. to about 95° C. More preferably, however, the reaction temperature is at a temperature in a range of from about 60° C. to about 85° C. and most preferably, in a range of from about 65° C. to about 80° C. Also, where a high energy radiation source, such as gamma ray radiation is used, the polymerization reaction may be conducted as low as about ambient temperature, for example about 20° C.

The polymerization reaction time is also primarily dependent on the type of initiator means used and its concentration. However, other factors affecting the desired reaction time include the type of monomer and its concentration, and the depth of the MCX mixture. Also, once a polymerization reaction is initiated, typically, it will not terminate in response to a sharp temperature drop. For example, once the MCX mixture is exposed to the desired initiation temperature, the polymerization reaction will proceed for some time thereafter, depending on the reaction temperature selected and the time period that the MCX mixture is exposed to the selected temperature (i.e., heat exposure period). Also, we have discovered that higher initiator concentrations generally produce residual monomer concentrations of about 200 ppm or less. However, these higher initiator concentrations are more likely to promote premature polymerization unless the temperature is kept sufficiently below 40° C. Accordingly, it is important to maintain the MCX mixture below 40° C. to reduce premature polymerization.

The time period that the MCX mixture is exposed to the selected reaction temperature may be in a range from as low as about 1 minute to as high as about 24 hours. For example, where an MCX mixture having a clay to monomer ratio of about 2:1 is pressed into a porous substrate to a depth of about 2–3 mm, potassium persulfate is used as a thermal initiator and the selected temperature is about 80° C., the duration of the heat exposure period is preferably in a range of from about 2 minutes to about 60 minutes. More preferably, under similar conditions, the heat exposure period is in a range of from about 2 minutes to 45 minutes and, most preferably, in a range from about 3 minutes to about 30 minutes.

Examples of redox systems include, without limitation, persulfate/bisulfite, persulfate/thiosulfate, persulfate/ascorbate, hydrogen peroxide/ascorbate couples, and combinations thereof. Typically, additional heat is not required when using a redox systems initiator because the reactions are often exothermic, so such systems can work effectively at temperatures in a range of from about the freezing point of the MCX mixture to the boiling point of the mixing fluid. Typically, the temperature is ambient, about 20° C.

Alternatively, polymerization may be initiated by electromagnetic radiation having a wavelength below about 10 nm such as, for example, without limitation, by gamma rays, X-rays, or high energy sub-atomic particles. In such a case, the polymerization reaction is typically conducted at ambient temperatures. However, the temperature can be higher or lower.

However, it is well known to those skilled in the art that UV radiation, with wavelengths ranging from about 200 nm to 390 nm is not suitable for polymerization initiation of the MCX mixture because the clay will interfere with UV light's ability to penetrate into the sample, and thereby initiate the polymerization reaction, even with a photo-initiator present. More specifically, it is believed that the clay preferentially absorbs the UV light, thereby inhibiting the UV light's effectiveness as an initiator means.

Optionally, once polymerized, all or a portion of the mixing fluid remaining in the NPC alloy product may be removed, for example by desiccating at room temperature or oven-drying. If oven-dried, the composite should be dried at a temperature that does not adversely affect the properties or characteristics of the product, for example, at a temperature less than about 110° C.

The moisture content of the products made with an NPC alloy is dependent on the application and other factors. For example, a higher moisture content product provides greater flexibility and a lower initial permeability. But a lower moisture content product can have reduced transportation costs. Consequently, the desired moisture content will be determined by the environment in which the product will be used and maximum acceptable transportation costs.

Therefore, for a product with at least some flexibility, the moisture content is preferably in a range of from about 25% to about 75% by weight.

NPC Alloy

In use, the NPC alloy swells on contact with water as the alloy absorbs water. Because of the networked structure, the composite swells substantially as an integrated unit while only negligible amounts of clay, if any (i.e., substantially no clay), separate from the composite when it is immersed in water at a temperature in a range of from about 1° C. to about 60° C., whether the water is saline or not.

It will be understood by those skilled in the art that the degree to which the NPC alloy is networked will affect the alloy's capacity to absorb water. Of course, if insufficient cross-linking agent is used, the NPC alloy may become water soluble under certain conditions and the clay could then substantially separate from the alloy. On the other hand, if excessive amounts of cross-linking agent are used, the NPC alloy may be so inflexible that it is unable to absorb sufficient amounts water and thereby reach either the desired fluid permeability and/or water absorption performance.

In containment applications, a barrier made using the NPC alloy is often under a confining stress due to overburden. Under a standard effective confining stress of 20 kPa or 2.9 psi, the flux (i.e., the rate water travels at the specified pressure) of the composite is about $10^{-8}$ $m^3/m^2/s$ or less, as measured by ASTM 5887-95. As the confining stress increases with additional overburden, the hydraulic conductivity of the barrier will decrease because the barrier will become compressed.

The following non-limiting examples of embodiments of the present invention that may be made and used as claimed herein are provided for illustrative purposes only.

EXAMPLE 1

Effect of Clay to Monomer Ratio on Water Absorption Capacity

NPC Alloy Preparation

Seven MCX mixtures were prepared in the amounts shown in Table 1. Clay to monomer weight ratios ranged from 0.1 to 9.62 in the seven MCX mixtures. The clay used in the MCX mixtures was NATURAL GEL™, a natural swelling clay often referred to as Wyoming bentonite, commercially available from American Colloid. The monomer was acrylamide, obtained from Cytec, West Paterson, N.J. A Control sample was made using acrylamide monomer without added clay.

Water, sodium hydroxide (NaOH), sodium bicarbonate (NaHCO$_3$), EDTA, acrylamide, N,N'-methylene bisacrylamide (NBAM) and potassium persulfate (K$_2$S$_2$O$_8$) were mixed in a 250-mL HDPE bottle. The aqueous solution was mixed well, prior to addition of clay. Clay was added and mixed again to form a homogeneous MCX mixture. All MCX mixtures were viscous but fluid before polymerization.

TABLE 1

| Component | Control | Sample (g) | | | | | | |
| --- | --- | --- | --- | --- | --- | --- | --- | --- |
| | | 1 | 2 | 3 | 4 | 5 | 6 | 7 |
| Water | 79.98 | 72.5 | 98.778 | 74.4 | 291.153 | 74.4 | 151.23 | 91.91 |
| NaOH | 3.768 | 3.108 | 3.904 | 2.28 | 7.498 | 1.891 | 1.563 | 0.506 |
| NaHCO$_3$ | 0.931 | 0.802 | 0.931 | 0.60 | 0.204 | 0.468 | 0.323 | 0.105 |
| EDTA | 0.109 | 0.09 | 0.116 | 0.08 | 0.217 | 0.06 | 0.042 | 0.025 |
| Acrylamide | 25.073 | 21.028 | 24.871 | 15.00 | 50.00 | 7.72 | 10.042 | 2.294 |
| NBAM | 0.057 | 0.05 | 0.058 | 0.04 | 0.123 | 0.028 | 0.022 | 0.012 |
| K$_2$S$_2$O$_8$ | 0.21 | 0.183 | 0.217 | 0.132 | 0.418 | 0.085 | 0.088 | 0.032 |
| Clay | — | 2.121 | 8.368 | 7.502 | 50.22 | 15.389 | 30.00 | 22.029 |
| Total (g) | 110.128 | 99.882 | 137.243 | 100.034 | 399.833 | 100.041 | 193.31 | 116.913 |
| Clay: Monomer Ratio (wt) | 0 | 0.10 | 0.34 | 0.50 | 1.00 | 2.00 | 3.00 | 9.60 |

The Control and MCX mixtures were left in an oven overnight at 65° C. for polymerization. After polymerization, the Control and NPC alloys were transferred to glass dishes and dried at 105° C. for 48 hours.

Water Absorption Capacity (WAC) of NPC Alloys

Approximately 1 gm of each NPC alloy and the Control was placed in a 500 mL HDPE bottle with 400 ml distilled water. After 48 hours, free water was decanted off the swollen NPC alloy using a 115 mesh screen.

The swollen NPC alloy was weighed and the water absorption capacity (WAC) was calculated according to the following equation:

$$WAC = \frac{(H_2O \text{ Swollen } NPC \text{ Alloy Mass-Dried } NPC \text{ Mass})}{\text{Dried } NPC \text{ Alloy Mass}}$$

A projected WAC, WAC$_{prj}$, based on the Control WAC and clay content was also calculated according to the following equation:

$$WAC_{prj} = \left(\frac{\text{Parts Monomer}}{\text{Total Parts Monomer + Clay}} \times \text{Control } WAC\right) + \left(\frac{\text{Parts Clay}}{\text{Total Parts Monomer + Clay}} \times \frac{\text{Max. Est.}}{\text{Clay } Wac}\right)$$

where the Control WAC=352 and the Maximum Estimated WAC for clay=10. For example, where a 1:3 clay to monomer ratio is used to produce the NPC alloy, the NPC alloy's WAC$_{prj}$ is [(¾)×352]+(¼)10=266. Likewise, where a 2:1 clay to monomer ratio is used, the NPC alloy's WAC$_{prj}$ is [(⅓)×352]+(⅔)10=124.

Finally, the monomer WAC (WAC$_m$) was also calculated to determine the water absorption capacity based on the amount of monomer used to produce the polymer/clay alloy sample being tested. The WAC$_m$ was calculated according to the following equation:

$$WAC_m = \frac{(H_2O \text{ Swollen } NPC \text{ Alloy Mass-Dried } NPC \text{ Alloy Mass})}{\text{Mass of Monomer used to produce } NPC \text{ Alloy}}$$

The results are tabulated in Table 2.

TABLE 2

| Sample ID | | Control | 1 | 2 | 3 | 4 | 5 | 6 | 7 |
| --- | --- | --- | --- | --- | --- | --- | --- | --- | --- |
| Clay: Monomer Ratio | | 0.00 | 0.10 | 0.34 | 0.50 | 1.00 | 2.00 | 3.00 | 9.61 |
| WAC | g H$_2$O per g | 352 | 339 | 332 | 213 | 207 | 134 | 83 | 14 |
| WAC$_{prj}$ | polymer/clay alloy | | 321 | 266 | 238 | 181 | 124 | 96 | 42 |
| WAC$_m$ | g H$_2$O per g monomer in polymer/clay alloy | 421 | 441 | 472 | 364 | 414 | 403 | 349 | 250 |

As shown in Table 2, the WAC for NPC alloy Samples 1 and 2 is 339 and 332, respectively. This means that the NPC alloy absorbs 339 and 332 times its own weight in water for these two samples, respectively, versus a 352 WAC for the clay-free Control. Bentonite clay typically has a paste-like consistency up to a water absorption of 5 to 10 times its weight, after which the clay becomes dispersed in water to form a slurry. Consequently, because bentonite clay is not known as being highly water-absorbent on a per unit mass basis, as compared with a water-absorbent polymer, the drop in WAC shown in Table 2 with increasing clay to monomer ratio was a surprising and unexpected result.

For example, at a 1:1 ratio, those skilled in the art might have projected a WAC of just slightly more than 0.5×the Control's WAC because only half of the NPC alloy is networked polymer. So, taking into account the water absorption for clay alone (i.e., about 5–10), a 1:1 clay to monomer ratio in an NPC alloy would have been expected to be, at best, about ½ the Control's WAC (i.e., 176) plus 5 for the clay's expected water absorption for a $WAC_{prj}$ of 181. But Sample 4, with a 1:1 clay to monomer ratio, has a 207 WAC, which is 14.4% greater than expected. Similarly, a 2:1 clay to monomer ratio has a $WAC_{prj}$ of about 124, while Sample 5 produced a 134 WAC, which is 8.1% greater than expected. The general trend is that WAC, across a broad range of clay to monomer ratios, is substantially comparable, if not slightly improved versus the clay-free Control until a significantly high clay loading in the NPC alloy is reached. At a significantly high clay loading, it appears that the polymer loading is so low that the clay's inherent WAC is dominant.

This is a surprising and unexpected result, particularly at high clay to monomer ratios of 2:1 and 3:1. Ogawa et al ("Preparation of Montmorillonite—Polyacrylamide Intercalation Compounds and the Water Absorbing Property" *Clay Science* 7:243–251; 1989) suggest on pg. 250 that clay acts as a cross-linking agent. Thus, Ogawa et al suggest that clay would act in concert with a cross-linking agent in an MCX mixture to severely constrain a polymer formed from that mixture. Moreover, the results in Example 2 illustrate that a cross-linking agent concentration as low as about 0.1 wt. % can over cross-link a polymer, thereby substantially reducing its water absorption capacity. Thus, the sensitivity of WAC to excess cross-linking agent and Ogawa et al suggest that increasing the clay content would produce a highly constrained NPC alloy with inhibited WAC. Consequently, it is surprising and unexpected that using an MCX mixture with both a cross-linking agent and clay, for example, at a 2:1 clay to monomer ratio, would produce an NPC alloy with comparable or slightly better performance than the clay-free Control.

When calculated on the basis of an equivalent amount of acrylamide monomer used to produce an alloy, the $WAC_m$ of the polymer/clay alloys Samples 1–5 is similar to that of the Control sample. As mentioned above, monomers are more costly than clay. Thus, the $WAC_m$ results demonstrate the economic advantages of the NPC alloy.

Table 2 demonstrates that good WAC results were obtained for the composition described in Table 1 in a clay to monomer ratio of about 0.3 to about 3.0. The optimal clay to monomer ratio will depend on the intended use of the compositions falling within the scope of the claimed invention. For instance, beyond adjusting the clay to monomer ratio, as discussed more fully under Example 2, the cross-linking agent to monomer ratio can also be adjusted to increase or decrease the WAC to the desired level.

For example, when used for making a landfill liner, a WAC for the NPC alloy only needs to be high enough to ensure that the NPC alloy swells sufficiently to occupy any interstitial spaces that were not occupied by NPC alloy when the liner was formed. This degree of swelling will ensure that the liner has sufficiently low permeability to water and other fluids. For example, the WAC for an NPC alloy used in a landfill liner could be as low as about 5. Of course, a higher WAC up to about 500 could also be used in a landfill liner. However, a WAC significantly much higher than 50 could reduce the structural integrity of the alloy due to excess water.

Consequently, in personal care type applications, where structural integrity is likely to be a factor as well, a WAC in a range of from about 20 to about 100 would be most likely desired for an absorbent material made from the NPC alloy.

Accordingly, the above data illustrates that the unique polymer/clay alloy can provide effective water absorption. As well, the clay component in the NPC alloy provides a cost effective means to make an NPC alloy while delivering the water absorbing and/or permeability property performance desired for the intended use.

EXAMPLE 2

Effect of Cross-Linking Agent to Monomer Ratio on WAC

NPC Alloy Preparation

Three MCX mixtures were mixed in the amounts shown in Table 3. The cross-linking agent to monomer weight ratios ranged from $1.10 \times 10^{-3}$ to $9.41 \times 10^{-3}$ in the three MCX mixtures. The clay to monomer weight ratio was held constant at about 1:1. The clay used in the MCX mixtures was NATURAL GEL™. The monomer was a 1:4 (wt) mixture of acrylic acid (Aldrich) and acrylamide (Cytec).

Water, NaOH, sodium carbonate ($Na_2CO_3$), acrylic acid, acrylamide, NBAM and $K_2S_2O_8$ were mixed in the proportions shown in Table 3 in a 2-L Erlenmeyer flask. The aqueous solution was mixed well, prior to addition of clay. Clay was added and mixed again to form a homogeneous MCX mixture. All MCX mixtures were viscous but fluid before polymerization.

TABLE 3

| | Sample (g) | | |
|---|---|---|---|
| Component | 8 | 9 | 10 |
| Water | 1000 | 1000 | 1000 |
| NaOH | 10 | 10 | 10 |
| $Na_2CO_3$ | 12 | 12 | 12 |
| Acrylic Acid (AA) | 20 | 20 | 20 |
| Acrylamide (AM) | 80 | 80 | 80 |
| NBAM | 0.941 | 0.303 | 0.11 |
| $K_2S_2O_8$ | 0.6 | 0.6 | 0.6 |
| Clay | 99 | 105 | 105 |
| Total (g) | 1222.541 | 1227.903 | 1227.71 |
| NBAM/(AA + AM) Wt Ratio (× $10^3$) | 9.41 | 3.03 | 1.10 |

The MCX mixtures were left in an oven overnight at 65° C. for polymerization. After polymerization, the NPC alloys were transferred to glass dishes and dried at 105° C. for 48 hours.

Water Absorption Capacity (WAC) of Polymer/Clay Alloys

Approximately 1 gm of NPC alloy Sample 8 was placed in a 500 mL HDPE bottle with 400 ml distilled water. After 48 hours, free water was decanted off the swollen NPC alloy using a 115 mesh screen.

The swollen NPC alloy was weighed and the water absorption capacity (WAC) was calculated as described in Example 1. Samples 9 and 10 were treated in the same manner. The results are tabulated in Table 4.

The monomer WAC ($WAC_m$) was also calculated to determine the water absorption capacity based on the amount of monomer used to produce the NPC alloy sample being tested. These results are also tabulated in Table 4.

TABLE 4

| Sample | | 8 | 9 | 10 |
|---|---|---|---|---|
| NBAM/(AA + AM) Wt Ratio (× $10^3$) | | 9.41 | 3.03 | 1.10 |
| WAC | g $H_2O$ per g polymer/clay alloy | 145 | 281 | 281 |
| $WAC_m$ | g $H_2O$ per g monomer in polymer/clay alloy | 324 | 641 | 640 |

As shown in Table 4, the NPC alloy's WAC increases as the cross-linking agent to monomer ratio decreases from $9.41 \times 10^{-3}$ to $3.03 \times 10^{-3}$. However, it is believed that a further significant decrease in cross-linking agent to monomer ratio (e.g., to about $0.10 \times 10^{-3}$) would sufficiently reduce the mechanical strength of the NPC alloy's networked polymer and thereby limit NPC alloy's ability to absorb and retain water.

Of course, to the extent the polymer is not cross-linked, the polymer will dissolve in water. Also, at low levels of cross-linking, the polymer may fracture and become water-soluble. However, if the degree of cross-linking is too high, there is too much constraint on the polymer and its water absorption capacity is reduced.

Accordingly, the above data illustrates that the unique NPC alloy can provide effective water absorption. As well, controlling the cross-linking agent to monomer ratio, alone or in combination with the clay to monomer ratio, provides a means for designing the water absorbing and/or permeability property performance desired for the intended use.

EXAMPLE 3

SEM and X-Ray Analysis

The following SEM micrographs and X-ray analyses illustrate that (1) clay in the NPC alloy is chemically associated with the polymer, (2) clay does not become dissociated from the NPC alloy when the polymer is swollen, and (3) the reinforced NPC alloy composite can contain a significant amount of occluded water retained from manufacture.

Monomer/Clay Mixture Preparation

An MCX mixture was prepared as shown in Table 5. The clay used in the MCX mixture was NATURAL GEL™. The monomer was a 1:4 (wt) mixture of acrylic acid (Aldrich) and acrylamide (Cytec).

Water, NaOH, $NaHCO_3$, acrylic acid, acrylamide, NBAM and $K_2S_2O_8$ were mixed in a 10-L HDPE pail. The aqueous solution was mixed well, prior to addition of clay. Clay was added and mixed again to form a homogeneous MCX mixture. The MCX mixture was viscous but fluid before polymerization.

TABLE 5

| Component | Amount (g) |
|---|---|
| Water | 5009.9 |
| NaOH | 55.1 |
| $NaHCO_3$ | 51.5 |
| Acrylic Acid | 100.8 |
| Acrylamide | 400.5 |
| NBAM | 1.62 |
| $K_2S_2O_8$ | 12.8 |

TABLE 5-continued

| Component | Amount (g) |
|---|---|
| Clay | 1000.8 |
| Total (g) | 6633.02 |
| Clay to Monomer Ratio (wt) | 2.00 |

Reinforced NPC Alloy Composite Preparation

The MCX mixture was poured in a thickness of about 1.5 mm onto a 0.95 m×0.80 m piece of TERRAFIX®270R-A geotextile (Terrafix Geosynthetics Inc., Toronto, Ontario, Canada), as a reinforcing agent. A polyethylene cover sheet was placed on top of the MCX mixture and a vacuum pressure in a range of from about 16 to about 30 kPa was applied to the sample from the geotextile's opposing side. The MCX mixture was intimately distributed in and on the geotextile material by applying the vacuum.

The reinforced MCX mixture sample was put under an infrared heater at 80° C. for 8 minutes for polymerization to form a reinforced NPC alloy composite. The moisture content of the reinforced NPC alloy composite was about 75%.

Scanning Electron Microscopy (SEM)

The reinforced NPC alloy composite was examined using a JEOL Model No. JSM 6301 FXV Scanning Electron Microscope (SEM, Japan Electron Optics Limited, Japan) at the SEM Facility, Department of Earth & Atmospheric Sciences, University of Alberta, Edmonton, Alberta, Canada.

Samples were pretreated for SEM examination by placing the samples in a holder and immersing them in liquid nitrogen (i.e., about −196° C.). Once frozen, the samples were removed from the liquid nitrogen, using pliers or a knife, quickly torn or cut, as indicated below, to obtain a cross-sectional perspective of the sample. The samples were then quickly transferred to the SEM vacuum chamber, where they were warmed to −40° C. to sublime any surface ice crystals. Next, the samples were placed in a coating chamber where a thin layer of gold was applied to the sample to increase electrical conductivity. The samples were then returned to the SEM vacuum chamber for examination. The samples were maintained at or near liquid nitrogen temperature during the gold coating and subsequent SEM examination. This was done so that the structure of the sample would be preserved. The samples contained considerable moisture and thus had to be maintained in a frozen state for the SEM to operate properly.

Figure 2:
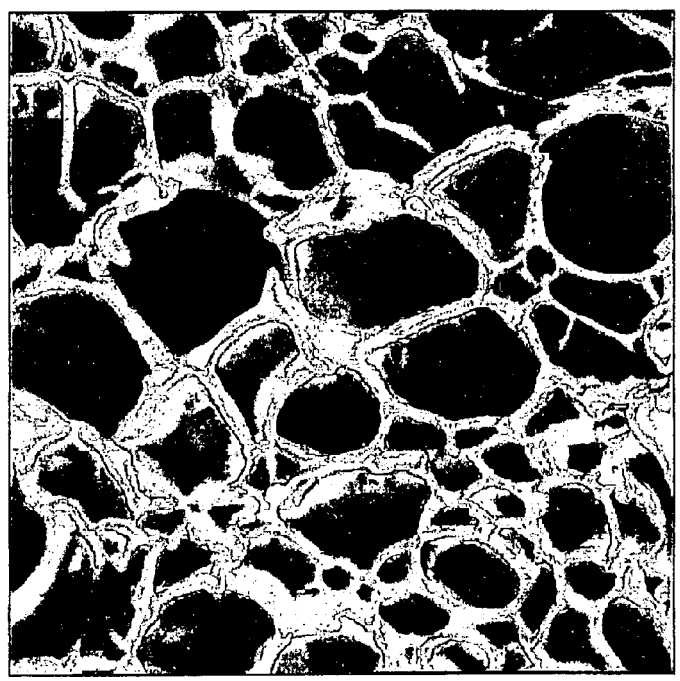
FIG. 2 is an SEM micrograph of a hydrated polymer used for comparison in Example 3, at a magnification of 7000×.
Figure 3:
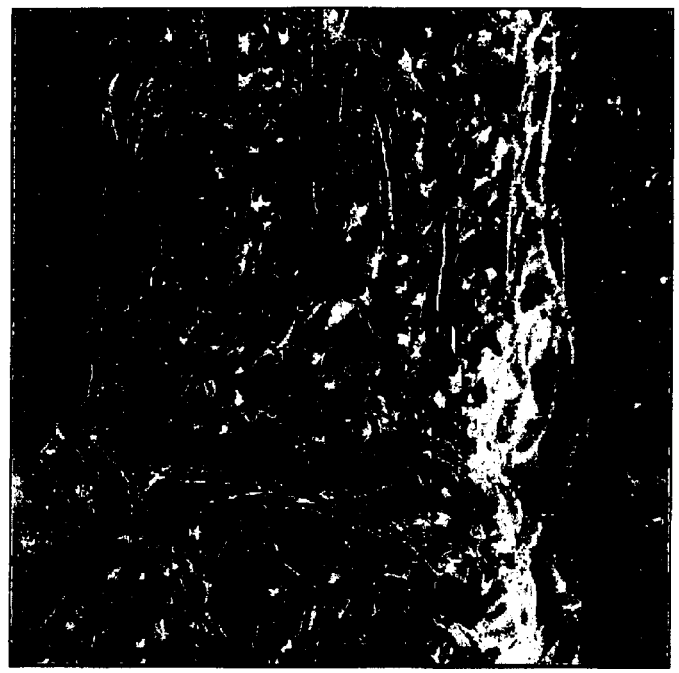
FIG. 3 is an SEM micrograph of a cross-section of a reinforced networked polymer/clay alloy composite produced in Example 3, at a magnification of 50×.
Figure 4:
FIG. 4 is an SEM micrograph of a cross-section of a reinforced networked polymer/clay alloy composite produced in Example 3, at a magnification of 270×.
Figure 5:
FIG. 5 is an SEM micrograph of a cross-section of a water-swelled reinforced networked polymer/clay alloy composite produced in Example 3, at a magnification of 500×.
Figure 6:
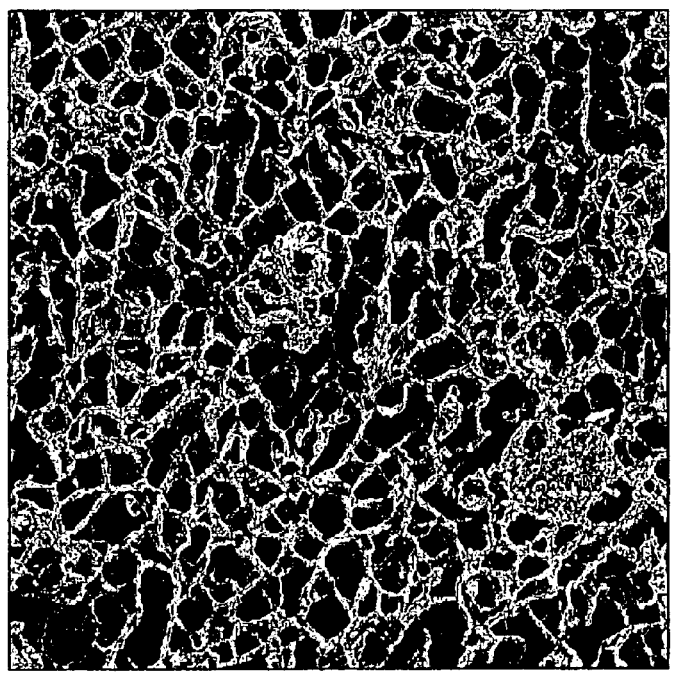
FIG. 6 is an SEM micrograph of a cross-section of a water-swelled reinforced networked polymer/clay alloy composite produced in Example 3, at a magnification of 4500×.

The sample in FIGS. 3 and 4 was cut with a knife prior to mounting. Both micrographs show the cut edges of fibers of the reinforcing agent. Particles seen in FIG. 4 are fragments from the cutting step in preparing the sample for SEM examination. The sample in FIGS. 5 and 6 was severed with a pair of pliers, instead of a knife, prior to mounting. FIG. 5 shows the fractured edges of fibers of the reinforcing agent and other fragments produced by fracturing. The SEM micrographs of FIGS. 1 to 7 are discussed in Table 6.

Discussion of SEM Micrographs

In summary, the SEM micrographs illustrate that (1) clay in the NPC alloy is chemically associated with the polymer, (2) clay does not become dissociated from the NPC alloy when the polymer is swollen, and (3) the reinforced NPC alloy composite can contain a significant amount of occluded water retained from manufacture.

TABLE 6

| FIG. # | Magnification | Description | Observations |
|---|---|---|---|
| 1 | 140X | Comparative. Top plan perspective of reinforcing agent without NPC alloy. | |
| 2 | 7000X | Comparative. Potassium acrylate cross-linked and polymerized without clay. No reinforcing agent. Sample immersed in water for 10 minutes prior to SEM. | Swollen polymer has crater-like open-cell structure. The open cells were previously occupied by occluded water, which was removed by SEM pre-treatment procedures. It is expected that acrylamide/sodium acrylate copolymer would behave in a similar manner. |
| 3 | 50X | Reinforced NPC alloy composite. Sample dried from the original 75 wt. % moisture to about 25–50 wt. % with ambient drying conditions over a 2 week period. The NPC alloy shrank around the reinforcing agent fibers. The shrinkage indicates the volume occupied by previously occluded water. | Illustrates NPC alloy intimately integrated with reinforcing agent. Also illustrates thin layer of NPC alloy (right-hand side of micrograph) integrated with NPC alloy in reinforcing agent; i.e., not a laminate structure. |
| 4 | 270X | Same as FIG. 3 | No individual clay particles can be seen in the SEM micrographs, illustrating that the clay particles are chemically associated with polymer in NPC alloy, even at clay to monomer ratio of 2:1. |
| 5 | 500X | Reinforced NPC alloy composite immersed in water for 10 minutes prior to SEM. | Illustrates how swollen NPC alloy expands to conform to and substantially occupy interstitial spaces in reinforcing agent. |
| 6 | 4500X | Same as FIG. 5. | Illustrates that clay particles are chemically associated with polymer in NPC alloy. No free clay particles are seen, therefore indicating that the clay does not dissociate from NPC alloy when water-swollen. Swollen NPC alloy has open-cell structure, similar to polymer without clay (FIG. 2). Also, the degree of occluded water is substantially similar to polymer without clay (FIG. 2), therefore indicating that clay even at high loading does not have a disproportionately detrimental effect on NPC alloy's swelling capacity versus a clay-free water absorbing polymer. |
| 7 | 650X | Comparative. Same monomer/cross-linking agent mixture as used for FIG. 5 sample, but without clay. Immersed in water for 10 minutes prior to SEM. | Swollen polymer fills interstitial spaces in reinforcing agent in same manner as NPC alloy in FIG. 5. Open-cell structure of polymer without clay similar to that of the clay-based sample shown in FIG. 10. Comparison to FIG. 5 illustrates how the clay is (a) integrated in the NPC alloy and (b) does not have a disproportionately detrimental effect on NPC alloy's swelling capacity. |

Figure 7:
FIG. 7 is an SEM micrograph of a cross-section of a water-swelled polymer, without clay, at a magnification of 650×.

As shown more clearly in the comparison between FIG. 5 (reinforced NPC alloy composite) and FIG. 2 (swollen polymer without clay) or FIG. 7 (swollen polymer without clay in reinforcing agent), the swollen NPC alloy open-cell structure is similar to that of clay-free polymers. Accordingly, the clay does not constrain the NPC alloy's water swelling capacity. In view of Ogawa et al (discussed more fully in Example 1, which suggests that clay acts as a cross-linking agent for making water absorbent polymers, this is a surprising and unexpected result. Also, in view of the cross-linking agent results in Example 2, which illustrate that a cross-linking agent concentration as low as about 0.1 wt. % can over cross-link a polymer, thereby substantially reducing its water absorption capacity, these results are most particularly surprising and unexpected at a relatively high clay to monomer ratio of 2:1.

X-Ray Analyses

The Energy Dispersive X-Ray (EDX) analysis device of the SEM collects signals from an area of 1 $\mu$m×1 $\mu$m at a penetration depth of about 1 $\mu$m. X-ray analysis was conducted at numerous sites on the sample in FIG. 6, including the NPC alloy at the center of FIG. 6. Consistently at each site, peaks appeared for gold (2.1, 8.5 keV), silicon (1.74 keV), aluminum (1.49 keV), sodium (1.04 keV), magnesium (1.25 keV), and iron (0.615, 6.40 keV). The gold peak was a result of the gold treatment for the SEM examination. The relative strengths and positions of the silicon and aluminum peaks in the EDX spectra were consistent with those expected for bentonite clay. All sites examined showed the presence of silicon, aluminum, sodium, magnesium and iron. This analysis shows that the NPC alloy is homogeneous throughout the sample, even at the 1 $\mu m^3$ level. Accordingly, the clay in the NPC alloy is chemically associated with the polymer.

EXAMPLE 4

Clay Migration Tests

This example illustrates that, when the reinforced NPC alloy composite is immersed in water, the NPC alloy swells with substantially no clay separating from the alloy.

NPC Alloy

An MCX mixture was prepared by mixing 40.51 g acrylic acid with 500 g water. 36.6 potassium hydroxide and 0.624 g NBAM were then added with stirring. After the potassium hydroxide was in solution, 24.39 g potassium carbonate was dissolved, followed by addition of 160.33 g acrylamide, 4.83 g potassium persulfate and 500 g water. 594.07 g of the monomer mixture was blended with 199.79 g bentonite clay in a flood blender to give a creamy suspension.

The MCX mixture was polymerized by heating in a 75° C. oven for 8 minutes.

This NPC alloy was labeled as Sample A in the clay migration tests.

Reinforced NPC Alloy Composite

A layer of the MCX mixture prepared above was poured onto a 2 cm×2 cm piece of TERRAFIX®270R-A geotextile. The MCX mixture was intimately distributed in and on the geotextile material by hand. The MCX mixture was polymerized in the reinforcing agent by heating in a 75° C. oven for 8 minutes.

This reinforced NPC composite was labeled as Sample B in the clay migration tests.

Comparative Sample C—No Polymerization Initiator, No Cross-linking Agent

The monomer/clay mixture for Comparative Sample C was prepared by mixing 18.7 g acrylic acid, 6.1 g sodium hydroxide, 34.9 g clay and 18 g water to form a viscous paste. The paste was then forced into a 2 cm×2 cm piece of TERRAFIX® 270R-A. The monomer/clay mixture could not be embedded into the geotextile at 100 kPa. So, one of the inventors, weighing about 80 kg, placed a piece of PLEXIGLAS™ on top of the sample and stood on it while rocking back and forth. About half of the monomer/clay mixture was forced into the fabric using this method. No polymerization initiator or cross-linking agent was added to the monomer/clay mixture.

The sample was dried in an oven at 75° C. for one hour.

Comparative Sample D—No Polymerization Initiator

A monomer/clay mixture was prepared by mixing 79.89 g acrylamide, 20.56 g acrylic acid, 0.3 g NBAM as cross-linking agent, 9.995 sodium hydroxide, 9.962 g sodium carbonate, and 1000 g water. 552.8 g of the monomer mixture was blended with 100.55 g bentonite clay in a flood blender to give a creamy suspension. No polymerization initiator was added to the monomer/clay mixture.

A layer of the monomer/clay mixture was poured onto a 2 cm×2 cm piece of TERRAFIX® 270R-A geotextile. The mixture was intimately distributed in and on the geotextile material by hand. The monomer/clay mixture was heated in a 70° C. oven for 1 hour in the reinforcing agent.

This sample was labeled as Sample D in the clay migration tests.

Comparative Sample E—Pre-Formed Oligomer (MW 2,000)

Comparative Sample E was prepared by mixing 6.5 g pre-formed polyacrylic acid, 1.6 g sodium hydroxide, 26 g water and 10.70 g clay. The polyacrylic acid, having a molecular weight of 2,000, was obtained from Aldrich Chemical Co.

A layer of the pre-formed oligomer/clay mixture was poured onto a 2 cm×2 cm piece of TERRAFIX® 270R-A geotextile. The pre-formed oligomer/clay mixture was intimately distributed in and on the geotextile material by hand. The sample was dried in an oven at 75° C. for one hour.

Comparative Sample F—Pre-Formed Polymer (MW 450,000)

Comparative Sample F was prepared by mixing 4.74 g pre-formed polyacrylic acid, 1.44 g sodium hydroxide, 96 g water and 11.52 g clay. The polyacrylic acid, having a molecular weight of 450,000, was obtained from Aldrich Chemical Co.

A layer of the pre-formed polymer/clay mixture was poured onto a 2 cm×2 cm piece of TERRAFIX® 270R-A geotextile. The mixture was intimately distributed in and on the geotextile material using a wooden rolling pin. The sample was dried in an oven at 75° C. for one hour.

Clay Migration Test Procedure

Each of the samples was placed in a glass bottle. 100 mL deionized water at room temperature (about 20° C.) were then poured into the bottle.

The bottle was left standing without disturbance at room temperature. The sample was observed at 3 hours and 22 hours after addition of water, as described in Table 7.

TABLE 7

| Sample | Description of Sample | Observations |
|---|---|---|
| A | MCX mixture: acrylamide, sodium acrylate, cross-linking agent, persulfate polymerization initiator, and clay.<br>The MCX mixture was polymerized @ 75° C. for 8 minutes. | After 3 hours, the sample had swelled considerably. After 22 hours, there was some additional swelling of the NPC alloy. The swelled NPC alloy was puffy in appearance. The clay remained as an integral part of the NPC alloy. (see FIGS. 8A and 8B). Substantially no clay separated from the NPC alloy after 22 hours of immersion time. |
| B | MCX mixture: acrylamide, sodium acrylate, cross-linking agent, persulfate polymerization initiator, and clay.<br>The MCX mixture was pressed into a fabric and polymerized in a fabric @ 75° C. for 8 minutes. | After 3 hours, the sample had swelled considerably. After 22 hours, there was some additional swelling of the NPC alloy. The swelled NPC alloy was puffy in appearance. Both the fabric and clay remained as an integral part of the NPC alloy. (see FIGS. 9A and 9B). Substantially no clay separated from the |

TABLE 7-continued

| Sample | Description of Sample | Observations |
|---|---|---|
| | | NPC alloy after 22 hours of immersion time. |
| C | Comparative. Monomer/clay mixture: acrylic acid, NaOH, water and clay. No polymerization initiator or cross-linking agent was used. The monomer/clay mixture was pressed into a fabric and dried @ 75° C. for one hour. | After 3 hours, the acrylic acid and sodium acrylate dissolved in the water. The clay had migrated off the fabric and swelled at the bottom of the test bottle. There was no change after 22 hours. |
| D | Comparative. Monomer/clay mixture: acrylamide, acrylic acid, NaOH, NBAM (cross-linking agent), water and clay. No polymerization initiator was used. The monomer/clay mixture was pressed into a fabric and heated for one hour @ 70° C. | After 3 hours, the acrylamide and sodium acrylate dissolved in the water. The clay had migrated off the fabric and dispersed in the water. There was no change after 22 hours. |
| E | Comparative. A pre-formed polyacrylic acid (MW = 2000) was mixed with clay and pressed into a fabric. | After 3 hours, the polyacrylic acid dissolved in the water. The clay migrated off the fabric and dispersed in the water. There was no change after 22 hours. (see FIGS. 10A and 10B) |
| F | Comparative. A pre-formed polyacrylic acid (MW = 450,000) was mixed with clay and pressed into a fabric. | After 3 hours, the polyacrylic acid dissolved in the water and some clay had migrated off the fabric. After 22 hours, the remaining clay had migrated off the fabric and swelled at the bottom of the bottle. |

Line drawings were prepared from some of the photographs taken during the clay migration tests summarized in Table 7.

Figure 8B:
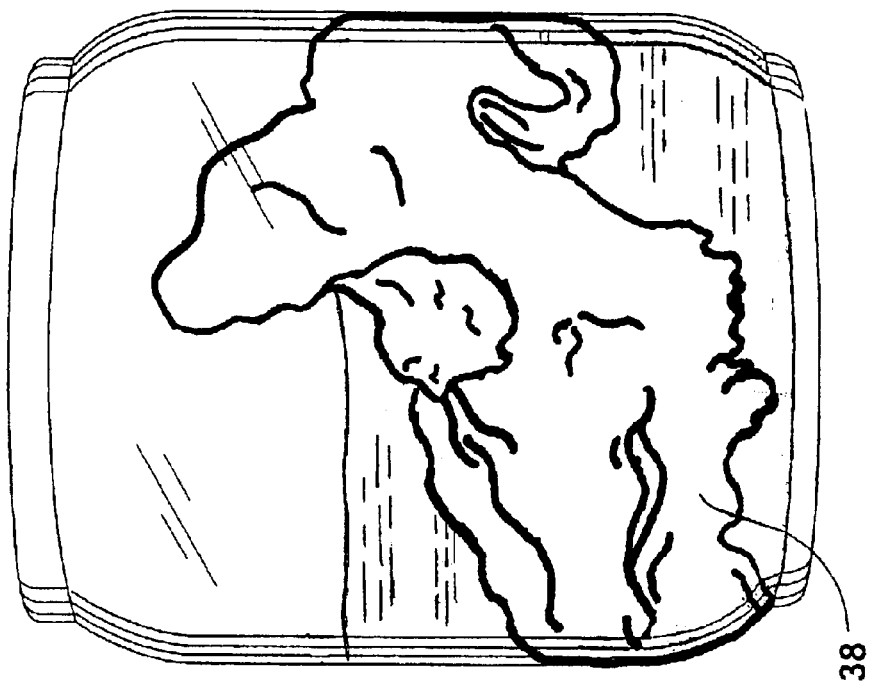
FIGS. 8A and 8B are drawings based on photographs taken of Sample A in Example 4 prior to immersion (8A) and after 3 hours immersion in deionized water (8B)
Figure 8A:
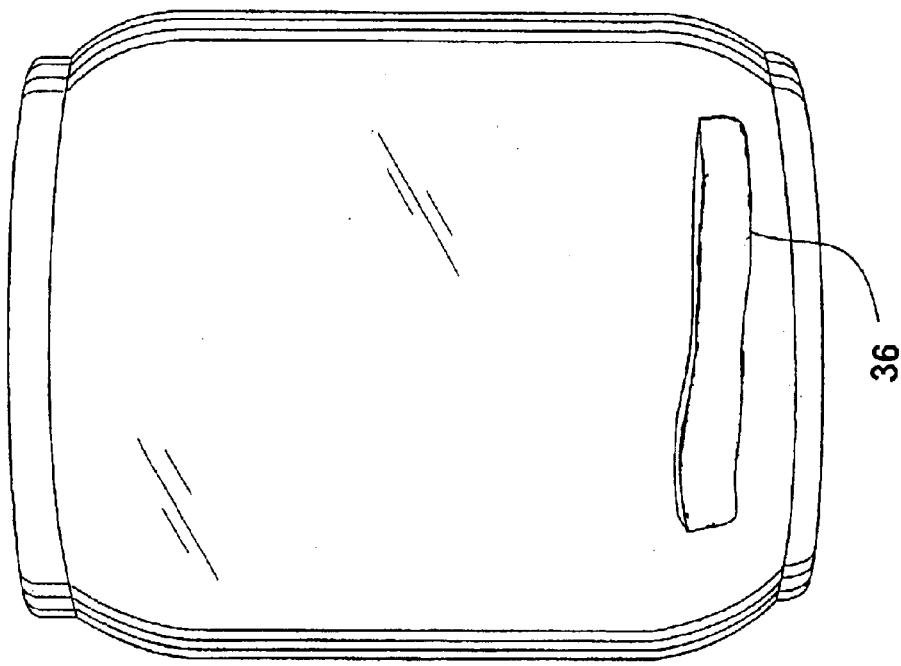

Sample A was an NPC alloy. FIG. 8A illustrates the NPC alloy 36 prior to immersion in deionized water. FIG. 8B illustrates the sample after 3 hours immersion in deionized water. The swelled NPC alloy 38 had a puffy appearance. Substantially no clay separated from the composite.

Figure 9B:
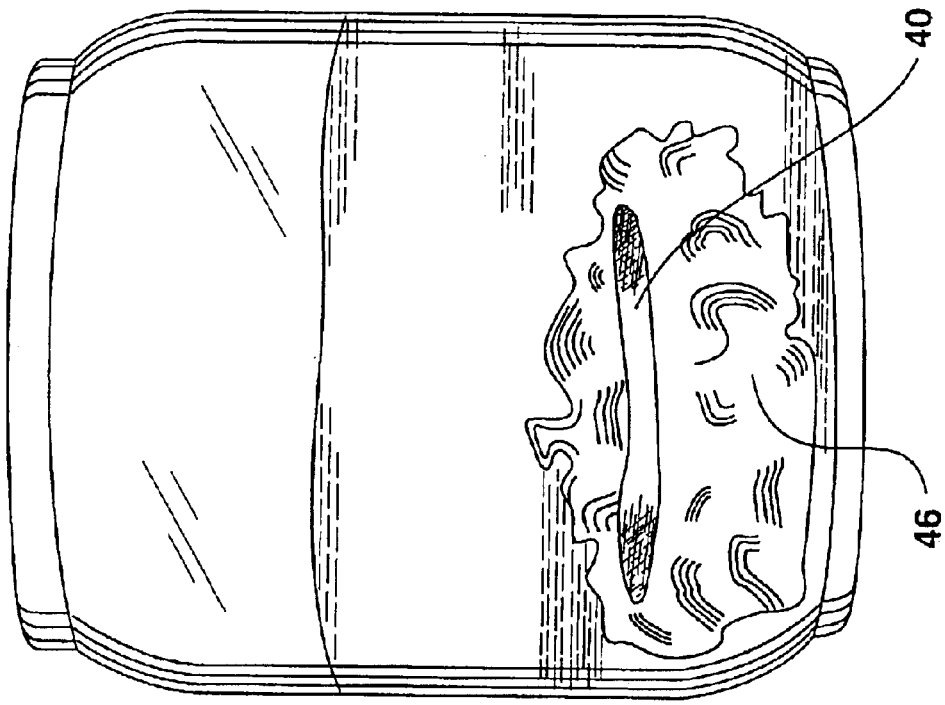
FIGS. 9A and 9B are drawings based on photographs taken of Sample B in Example 4 prior to immersion (A) and after 3 hours immersion in deionized water (9B)
Figure 9A:
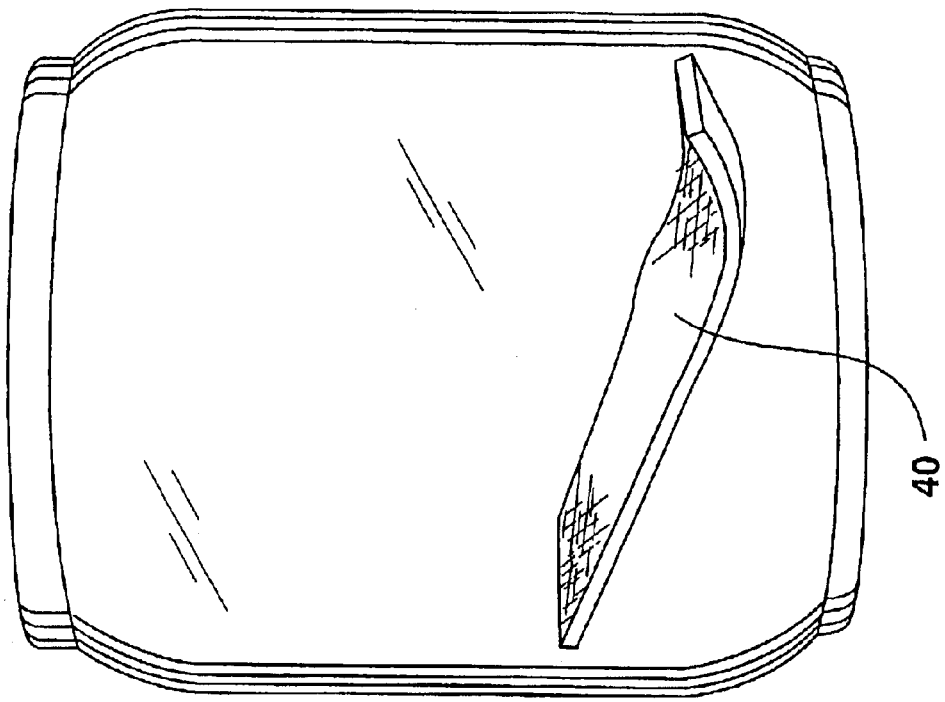

Sample B was a reinforced NPC alloy composite. FIG. 9A illustrates Sample B prior to immersion in deionized water. The NPC alloy is in the reinforcing agent 40. FIG. 9B illustrates the sample after 3 hours immersion in deionized water. The swelled NPC alloy 46 had a puffy appearance. Substantially no clay separated from the composite.

Figure 10B:
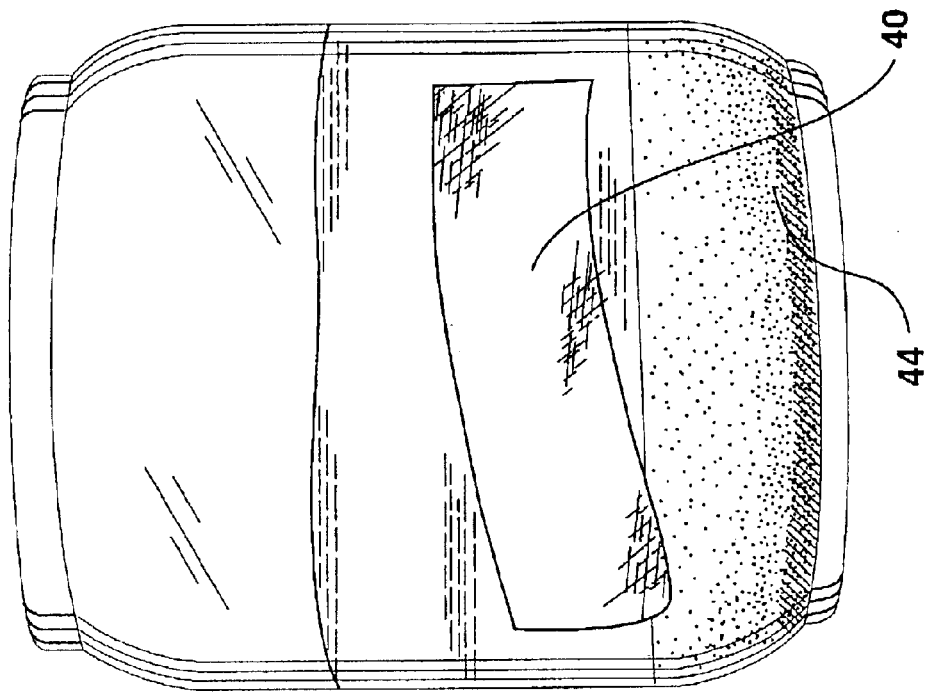
FIGS. 10A and 10B are drawings based on photographs taken of Sample E in Example 4 prior to immersion (10A) and after 3 hours immersion in deionized water (10B).
Figure 10A:
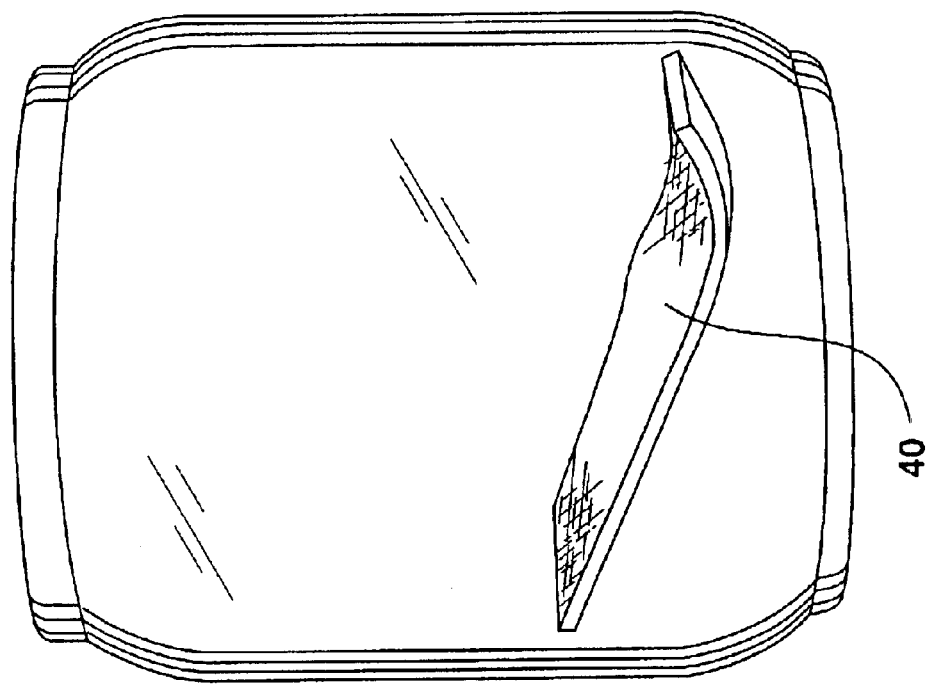

FIG. 10A illustrates Comparative Sample E prior to immersion in deionized water. The pre-formed polymer and clay mixture is in the reinforcing agent 40. FIG. 10B illustrates the sample after 3 hours immersion in deionized water. The polymer had dissolved in water and the clay 44 migrated off the reinforcing agent 40 and dispersed in the water. Some settling of the clay 44 is observed at the bottom of the bottle.

The results in Table 7 and FIGS. 8B and 9B illustrate how the clay is an integral part of the NPC alloy. Moreover, the results demonstrate how the NPC alloy is an integral part of the composite. In all of the comparative samples, clay migrates from the mixture and/or the reinforcing agent. Also, monomer and pre-formed polymer mixture migrate from the reinforcing agent. This is shown more clearly in FIG. 10B.

The NPC alloy remains substantially intact on exposure to deionized water at about 20° C. Specifically, substantially no clay separates from the NPC alloy. Moreover, the alloy is expected to exhibit substantially similar performance in deionized water in a temperature range of about 1° C. to about 60° C. This represents a significant improvement over the conventional techniques.

EXAMPLE 5

Residual Monomer Content

One concern about using acrylamide as a monomer for preparing an NPC alloy is the leaching of any residual monomer. The FDA limit for leachable acrylamide in polyacrylamide is 0.05% (500 ppm, 500 µg/g) when the polyacrylamide is used in treatment of potable water and for paper and paperboard for food contact applications (EPA/600/X-85/270 July 1985, PB88–170824).

This example provides residual monomer data for a polymer and an NPC alloy. Generally, the amount of residual monomer is dependent on initiator concentration, reaction time, and reaction temperature. For example, residual monomer content generally decreases with increased temperature, increased reaction time and increased initiator concentration.

Sample Preparation

A monomer mixture was prepared by mixing 20 g acrylic acid, 80 g acrylamide, 10 g sodium hydroxide, 12 g sodium carbonate, and 0.6 g potassium persulfate in 1000 mL water. The monomer mixture was divided into three parts and NBAM was added as a cross-linking agent at 0.1%, 0.3% and 0.9%, by weight, respectively. Each of the three monomer mixtures was sub-divided into three parts. Clay was added to some of the mixtures in an amount of about 1:1 monomer to clay or about 1:2 monomer to clay, as shown in Table 8. The MCX mixtures were blended in a food blender to produce a smooth, homogeneous mixture.

Samples of the monomer and MCX mixtures were transferred to plastic beakers and placed in an 80° C. oven for one hour for polymerization. The samples were removed from the oven and allowed to cool to room temperature. The samples were dried at 95° C. for a couple of days.

Residual Monomer Analysis

The residual acrylamide monomer was analyzed by EPA Method 8316 entitled "Acrylonitrile, Acrylamide and Acrolein by High Performance Liquid Chromatography (HPLC)."

A weighed sample of dried polymer or polymer/clay alloy (1–2 g) was placed in a polyethylene beaker with about 200 mL water and allowed to stand overnight at room temperature (about 20°) overnight. The polymer and NPC alloy samples swelled and absorbed some of the water. The remaining water was decanted from each swollen polymer and NPC alloy and analyzed for acrylamide content. The results are presented in Table 15.

TABLE 8

| Sample | Monomer Mixture (wt.) | Monomer: Clay (wt.) | Leached Acrylamide ppm ($\mu$g/g) polymer) |
|---|---|---|---|
| 8 | 20% Acrylic Acid, 80% Acrylamide, 0.1% NBAM | No Clay | 13.1 |
| 9 | 20% Acrylic Acid, 80% Acrylamide, 0.3% NBAM | No Clay | 128 |
| 10 | 20% Acrylic Acid, 80% Acrylamide, 0.9% NBAM | No Clay | 22 |
| 11 | 20% Acrylic Acid, 80% Acrylamide, 0.3% NBAM | 1:1 | 108 |
| 12 | 20% Acrylic Acid, 80% Acrylamide, 0.9% NBAM | 1:1 | 7596 |
| 13 | 20% Acrylic Acid, 80% Acrylamide, 0.3% NBAM | 1:2 | 90.1 |

The amount of leached acrylamide, leached by water from the dried polymer and NPC alloy samples, was well below the FDA limit of 500 ppm for all samples except one. Sample 12 resulted in a very high leached acrylamide concentration. Because of the inordinately high residual monomer, it appears that Sample 12 did not polymerize properly. Thus, Sample 12 is an aberrant data point, especially in view of the Sample 11 result, based also on a 1:1 MCX mixture, but with only 108 ppm residual acrylamide, and the Sample 9 result, a clay-free, monomer, cross-linking agent mixture, but with only 128 ppm residual acrylamide.

It was expected that polymerization may not proceed as extensively and, therefore, the amount of leached acrylamide would be greater, for samples containing clay, especially at higher amounts of clay. Surprisingly, however, as shown in Table 8, the amount of leached acrylamide was similar for Samples 11 and 13 (0.3% NBAM, 1:1 and 1:2 monomer to clay, respectively) and Sample 9 (0.3% NBAM, no clay).

This and the other examples presented herein demonstrates the advantages of the NPC alloy for use in fluid barrier applications and water absorbency applications.

Preferred compositions and processes for practicing the invention have been described. It will be understood that the foregoing is illustrative only and that other embodiments of the process for producing an NPC alloy can be employed without departing from the true scope of the invention defined in the following claims.

What is claimed is:

1. A process for producing a networked polymer/clay alloy, comprising the steps of:
  (a) preparing a monomer/clay mixture slurry by mixing at least a monomer, clay particles, a cross-linking agent, and a mixing fluid in a vessel;
  (b) exposing the monomer/clay mixture slurry to a thermal initiator means comprising at least one thermal initiator and thermal energy, wherein exposing the monomer/clay mixture slurry to the thermal initiator means comprises:
    (i) mixing, in any order, the at least one thermal initiator with at least the monomer, clay particles, the cross-linking agent and the mixing fluid so that the monomer/clay mixture slurry is exposed to the thermal initiator;
    (ii) exposing the monomer/day mixture slurry to a thermal energy source at a temperature in a range from about 400° C. to about 95° C.; and
  (c) polymerizing the monomer/clay mixture slurry so that a networked polymer/clay alloy is formed.

2. The process of claim 1, wherein the thermal initiator is selected from the group consisting of free radical initiators, carbanions, carbonium ions, and combinations thereof.

3. The process of claim 2, wherein the free radical initiator is selected from the group consisting of (a) alkali metal salts of sulfite, bisulfite, persulfate and benzoyl peroxide; (b) ammonium salts of sulfite, bisulfite, persulfate and benzoyl peroxide; (c) 2,2'-azobis(2-amidinopropane)-dihydrochloride and 2,2'azobis(4-cyanopentanoic acid); and combinations thereof.

4. The process of claim 1, wherein the mixing fluid is selected from the group consisting of water, alcohol, organic solvents, and combinations thereof.

5. The process of claim 1, wherein the clay particles are swelling clay particles selected from the group consisting of montmorillonite, saponite, nontronite, laponite, beidellite, iron-saponite, hectorite, sauconite, stevensite, vermiculite and combinations thereof.

6. The process of claim 1, wherein the clay particles are non-swelling clay particles selected from the group consisting of kaolin minerals, serpentine minerals, mica minerals, chlorite minerals, sepiolite, palygorskite, bauxite, silica and combinations thereof.

7. The process of claim 1, wherein the weight ratio of clay to monomer in the monomer/clay mixture slurry is in a range of from about 0.05:1 to about 19:1.

8. The process of claim 1, wherein the weight ratio of clay to monomer in the monomer/clay mixture slurry is in a range of from about 0.5:1 to about 3:1.

9. The process of claim 1, wherein the monomer has the following general formula:

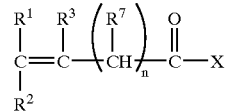

wherein X is selected from the group consisting of OM, OR$^4$ and NR$^5$R$^6$, M is an alkali or alkaline earth metal ion or NH$_4^{30}$, R$^1$, R$^2$, R$^3$, R$^5$, R$^6$ and R$^7$ are independently selected from the group consisting of H, CH$_3$, CH$_2$CH$_3$, CH$_2$CH$_2$CH$_3$, CH(CH$_3$)$_2$, CH$_2$CH$_2$CH$_2$CH$_3$, and CN, and OR$^4$ is selected from the group consisting of OH, OCH$_3$, OCH$_2$CH$_3$, OCH$_2$CH$_2$CH$_3$, OCH(CH$_3$)$_2$, OCH$_2$CH$_2$CH$_2$CH$_3$, OCH$_2$CH$_2$OH, and (OCH$_2$CH$_2$)$_m$OH, n=0 to about 10 and m=1 to about 10.

10. The process of claim 1, wherein the monomer is selected from the group consisting of acrylic acid, acrylamide, sodium acrylate, potassium acrylate, methacrylic acid, isopropylacrylamide, and combinations thereof.

11. The process of claim 1, wherein the cross-linking agent is selected from the group consisting of N,N'-methylene bisacrylamide, phenol formaldehyde, terephthalaldehyde, allylmethacrylate, diethyleneglycol diacrylate, ethoxylated trimethylolpropane triacrylate, ethylene carbonate, ethylene glycol diglycidal ether, tetraallyloxyethane, triallylamine, trimethylolpropanetriacrylate, and combinations thereof.

12. A product produced by the process of claim 1.
13. A product produced by the process of claim 2.
14. A product produced by the process of claim 3.
15. A product produced by the process of claim 4.
16. A product produced by the process of claim 5.
17. A product produced by the process of claim 6.
18. A product produced by the process of claim 7.
19. A product produced by the process of claim 8.
20. A product produced by the process of claim 9.
21. A product produced by the process of claim 10.
22. A product produced by the process of claim 11.

* * * * *